United States Patent [19]
Levin et al.

[11] Patent Number: 6,080,168
[45] Date of Patent: Jun. 27, 2000

[54] COMPRESSION PAD FOR LAPAROSCOPIC/ THORASCOPIC SURGERY

[76] Inventors: John M. Levin, 412 Fairview Rd., Narberth, Pa. 19072; Judy A. Smith, 15 Flourtown Rd., Plymouth Meeting, Pa. 19462

[21] Appl. No.: 08/919,983

[22] Filed: Aug. 28, 1997

[51] Int. Cl.⁷ ................................................. A61B 17/04
[52] U.S. Cl. ........................... 606/151; 606/127; 606/108
[58] Field of Search ..................... 606/127, 200, 606/108, 151

[56] References Cited

U.S. PATENT DOCUMENTS

| | | |
|---|---|---|
| 1,275,520 | 8/1918 | Bell . |
| 3,372,696 | 3/1968 | Rudie . |
| 3,863,639 | 2/1975 | Kleaveland . |
| 4,205,680 | 6/1980 | Marshall . |
| 4,964,417 | 10/1990 | Peters . |
| 5,074,867 | 12/1991 | Wilk . |
| 5,122,155 | 6/1992 | Eberbach . |
| 5,147,374 | 9/1992 | Fernandez . |
| 5,165,425 | 11/1992 | Vermot . |
| 5,197,493 | 3/1993 | Grier-Idris . |
| 5,209,243 | 5/1993 | Glassman . |
| 5,254,133 | 10/1993 | Seid . |
| 5,304,187 | 4/1994 | Green et al. . |
| 5,342,370 | 8/1994 | Simon et al. . |
| 5,366,460 | 11/1994 | Eberbach . |
| 5,370,650 | 12/1994 | Tovey et al. . |
| 5,375,588 | 12/1994 | Yoon . |
| 5,387,224 | 2/1995 | Semm . |
| 5,391,141 | 2/1995 | Hamilton . |
| 5,395,383 | 3/1995 | Adams et al. . |
| 5,396,906 | 3/1995 | Harrold . |
| 5,397,332 | 3/1995 | Kammerer et al. . |
| 5,403,343 | 4/1995 | Sugarbaker . |
| 5,405,360 | 4/1995 | Tovey . |
| 5,417,684 | 5/1995 | Jackson et al. . |

*Primary Examiner*—Michael Buiz
*Assistant Examiner*—Tina T D. Pham
*Attorney, Agent, or Firm*—Caesar, Rivise, Bernstein, Cohen & Pokotilow, Ltd.

[57] ABSTRACT

A reversibly expandable compression pad for compressing tissues and/or organs to provide a relatively unobstructed surgical field during laparoscopic surgery and/or thorascopic surgery. The compression pad is flexible enough to be deployed, manipulated and removed through a laparoscopic access tube, and is heavy enough to compress tissues and/or organs. The pad can also be used as a table on which to rest objects during surgery.

31 Claims, 3 Drawing Sheets

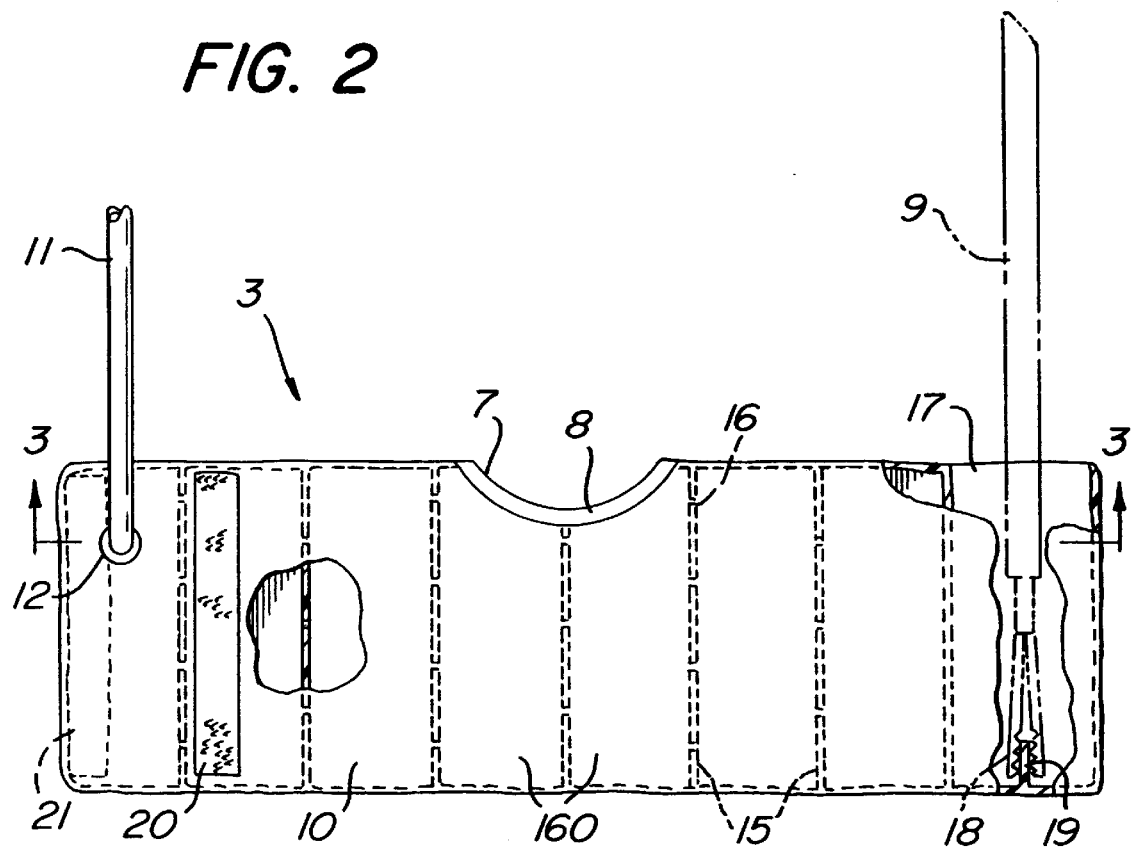
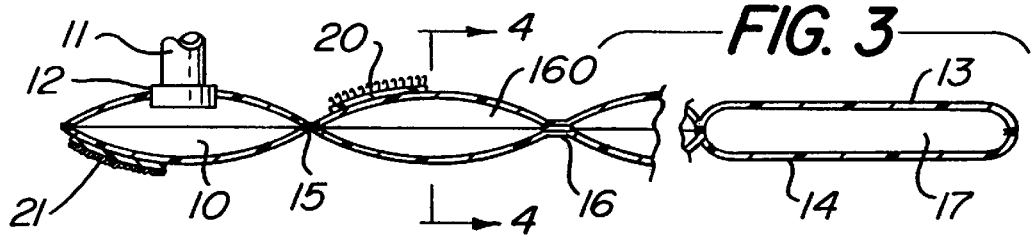
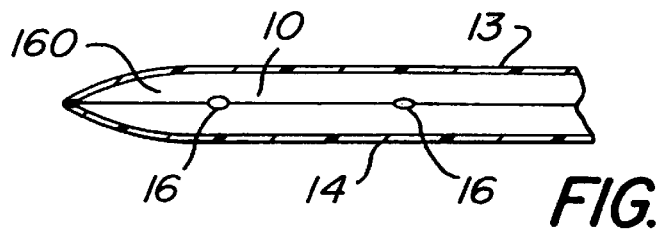

COMPRESSION PAD FOR LAPAROSCOPIC/THORASCOPIC SURGERY

BACKGROUND OF THE INVENTION

Surgeons are required to precisely distinguish between various tissues when performing surgery. A significant amount of time and effort in thoracic and abdominal cavity surgery is devoted to providing unobstructed access to the particular tissue that is being modified, removed and/or replaced. Surgical procedures benefit from an unobstructed surgical field, which provides the surgeon with good visibility of, and a clear path to, the tissues and/or organs of interest. Various means have been employed to create unobstructed surgical fields.

The "non-cutting" hand of the surgeon or a hand of a surgical assistant can, of course, be used to obtain a relatively unobstructed surgical field. However, this means for clearing the surgical field requires a free hand, which may not always be available or accessible to the surgical field. Moreover, the presence of an additional hand in the surgical field can be an impediment in itself.

Metal retractors and spatulas can be used in lieu of an additional hand in the surgical field, but still generally require a surgical assistant to hold the device. Moreover, retractors and spatulas are relatively inflexible, and thus must be removed from the surgical field relatively early in wound closure.

Surgical "fish" or "flounder" are said to provide some of the benefits of an additional hand without the drawbacks. For example, U.S. Pat. No. 4,964,417 to Peters discloses a fish-shaped wound closure device made of a flexible sheet material, adapted to be removably inserted under tissue adjacent to a surgical incision to cover and retain within the body cavity internal organs exposed by the incision.

Similarly, U.S. Pat. No. 3,863,639 to Kleaveland discloses a reversibly inflatable retainer device for temporarily retaining viscera inside the abdominal cavity of a patient during closure of an abdominal incision following surgery.

While the foregoing techniques and devices have been more or less effectively employed during conventional open surgical procedures in which large incisions are created, they are not adapted for use in laparoscopic/thorascopic surgery, wherein surgical procedures are conducted through at least one surgically created porthole into the patient's body.

The benefits from laparoscopic/thorascopic surgery are numerous. Large scars are eliminated, and the process in many instances is relatively bloodless and is much less traumatic to the patient than open surgery. The patient is ambulatory much sooner after laparoscopic/thorascopic surgery than after open surgery.

However, the limited means for accessing the surgical field during laparoscopic/thorascopic surgery require that instruments be adapted for deployment via tubes into the patient's body. Instruments must be narrow enough to be inserted into a patient without causing undue trauma. Moreover, the limited number of portholes cut into the body further limits access to the surgical field to as few as one or two instruments simultaneously.

As with open surgery, laparoscopic/thorascopic surgery requires a relatively unobstructed surgical field. In particular, the relatively free-floating intestines frequently obstruct the surgical field during abdominal cavity laparoscopies. Thus, there has been a need for a device that helps to provide an unobstructed surgical field for laparoscopic/thorascopic surgery.

All references cited herein are incorporated herein by reference in their entireties.

SUMMARY OF THE INVENTION

The instant invention addresses at least the foregoing deficiencies of the prior art by providing a compression pad for laparoscopic/thorascopic surgery which can be inserted through a laparoscopic/thorascopic surgery porthole or tube, expanded within the body cavity to compress tissues and/or organs and maintain a relatively unobstructed surgical field, and compressed, deflated or folded to a configuration that can be removed through the same passageway through which it entered.

The invention also provides a method for eliminating tissue obstructions from a surgical field within a body cavity of a patient during laparoscopic/thorascopic surgery, the method comprising inserting a surgical compression pad for laparoscopic/thorascopic surgery into the body cavity through an access tube into the body cavity, wherein the pad is flexible and expandable; expanding the pad to a shape that is too large to pass unchanged through the tube; and contacting tissue adjacent to the surgical field with the expanded pad to define a relatively unobstructed surgical field from which tissues and/or organs that are not involved in the surgical procedure are separated.

BRIEF DESCRIPTION OF THE DRAWINGS

The invention will be described in conjunction with the following drawings in which like reference numerals designate like elements and wherein:

FIG. 2 is a plan view of a particularly preferred embodiment of the invention, with portions of the top layer cut away to reveal underlying details;

FIG. 3 is a cross-sectional view through line 3—3 of FIG. 2;

FIG. 4 is a cross-sectional view through line 4—4 of FIG. 3;

DETAILED DESCRIPTION OF PREFERRED EMBODIMENTS

This disclosure focuses on laparoscopy procedures and tools as the preferred embodiment of the invention; however, the invention encompasses the use of the compression pads of the invention in any laparoscopic surgery and/or thorascopic surgery within a body cavity through tubes or trocars.

Figure 1A:
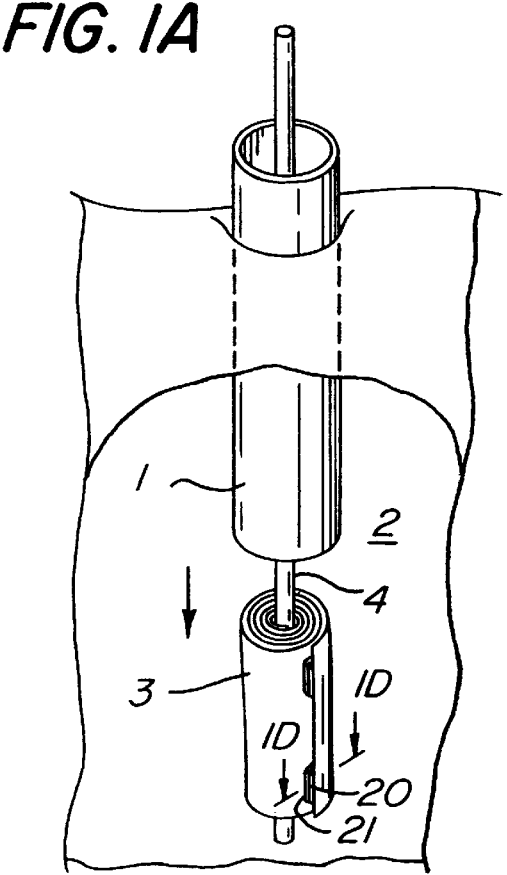
FIGS. 1A, 1B and 1C are somewhat idealized, sequential, fragmentary perspective views of an embodiment of the invention being deployed, as deployed and being removed, with a portion of the body partially cut away.
Figure 1B:
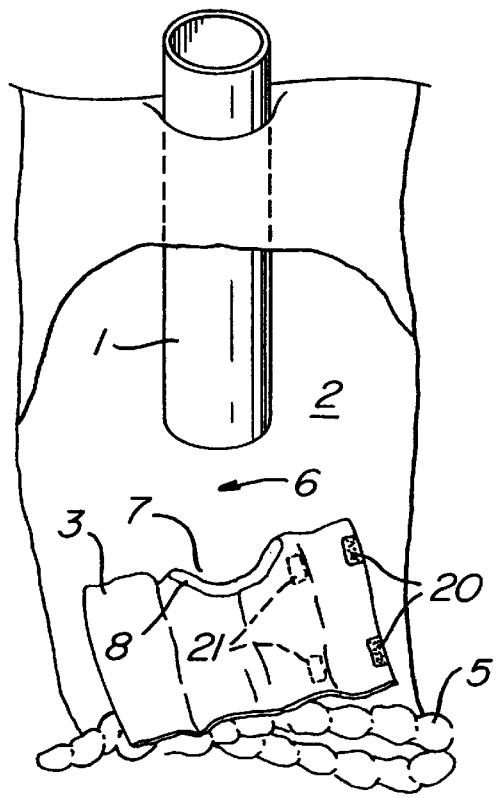
Figure 1C:
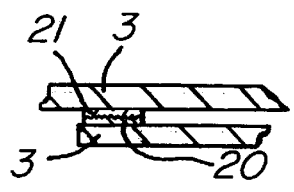

FIGS. 1A, 1B and 1C show a tube or trocar 1 inserted into a patient's body cavity 2 to act as an access port for a laparoscopic procedure into the body cavity 2. Preferably prior to operating on the tissues and/or organs of interest, a laparoscopic/thorascopic compression pad 3 is wound around a deployment tool 4 so as to fit through tube 1. After entering body cavity 2, pad 3 is unwound from tool 4 by rotating tool 4. The inertial mass of pad 3 can be sufficient to ensure that pad 3 unwinds from tool 4; however, unwinding can be facilitated by grasping pad 3 with a grasping tool (not shown in FIG. 1A), such as a forceps, which may be inserted through the same or a different tube/trocar.

As shown in FIG. 1B, the pad 3 unwinds to adopt a configuration providing a much larger surface area than in its wound configuration. Unwound pad 3 is sufficiently heavy to compress tissues and/or organs beneath it, such as the intestines 5, thus providing a relatively unobstructed surgical field 6.

Preferably, pad 3 is notched with an organ isolating notch 7 for better positioning within body cavity 2. The edge of notch 7 is preferably weighted with a strip of material 8, such as bismuth or lead, to cause the edge to be biased downwardly and assist in providing a relatively unobstructed surgical field.

In addition to its tissue and/or organ compressing function, pad 3 acts as a suction aid by preventing tissues and/or organs from blocking suction devices (not shown) used in laparoscopic/thorascopic surgery.

Pad 3 can also act as an internal table on which objects can be temporarily rested during surgery. Pad 3 can be provided with pockets, or the like, for temporarily restraining objects rested thereon. Such pockets or restraints could be used to store surgical instruments, which could be inserted into and/or removed from body cavity 2 separately from pad 3 and/or with pad 3.

Pad 3 is removed from body cavity 2 after completion of the essential object of the surgical procedure, and prior to closing. FIG. 1C shows one way of removing pad 3, wherein a grasping tool 9, such as, e.g., forceps, is used to grasp pad 3, and remove it from body cavity 2 through tube 1. In such a case, pad 3 must be sufficiently thin and flexible to be removed from body cavity 2 without injuring the patient. Suitable materials for such a pad 3 include rubber and biologically inert flexible synthetic resin materials, such as polyethylene or nylon, which are impermeable to microorganisms.

Alternatively, pad 3 can be removed from body cavity 2 by rewinding it about deployment tool 4 or another tool inserted through tube 1 and pulling the tool and pad 3 out of body cavity 2. Pad 3 can be rewound about the tool using solely the tool, or the tool in combination with a grasping tool (not shown). If only the tool is used to rewind pad 3, it is preferred that the tool and/or pad 3 include means for preventing pad 3 from sliding on the surface of the tool as the tool is rotated. Such means include frictional means, mechanical means, magnetic means and adhesive means.

Figure 1D:
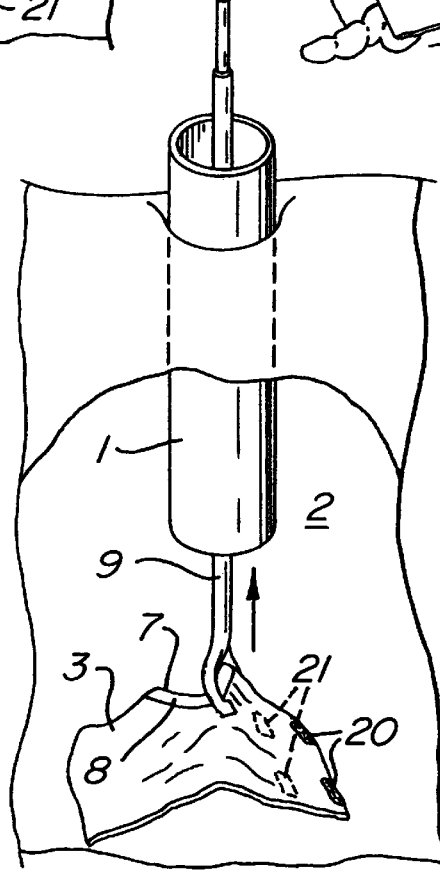
FIG. 1D is a cross-sectional view through line 1D—1D of FIG. 1A.

The tool and pad 3 can frictionally engage each other by providing at least one of them with a roughened surface. Preferably, the tool and pad 3 have opposing complementary portions of VELCRO® 20 and 21 attached thereto, as shown in detail in FIG. 1D, to facilitate insertion and removal of pad 3.

The tool and pad 3 can mechanically engage each other by, e.g., providing the tool with a slot for receiving an edge of pad 3, wherein the slot holds the edge while the tool is rotated. Alternatively, a grasping tool can be used to grasp a portion of pad 3, while the pad is wound about the tool by rotating the tool.

The tool and pad 3 can magnetically engage each other by providing a magnet on at least one of them. If the tool is metal, the magnet can be provided on pad 3. If pad 3 is metal, the magnet can be provided on the tool. If neither the tool nor pad 3 are metal, magnets of opposing polarity can be provided on the tool and pad.

The tool and pad 3 can adhesively engage each other by providing a physiologically compatible adhesive on at least one of them.

The construction of tube 1 is not particularly limited, and can be any tube suitable for accessing internal body cavities during laparoscopic/thorascopic surgery.

In the embodiment of the invention wherein pad 3 is removed by winding it around a tool, pad 3 can comprise, e.g., a physiologically acceptable film and/or woven material. In certain embodiments, ballast can be incorporated into pad 3 and/or attached to pad 3, to facilitate moving tissues and/or organs out of the surgical field. For example, metal shafts, particularly steel shafts, can be attached to pad 3 such that the shafts are parallel to deployment tool 4 when pad 3 is wound around tool 4. These shafts also affect the unwound structure of pad 3.

The construction of deployment tool 4 is not particularly limited, provided that the tool is sufficiently rigid and long to accomplish its purpose of deploying pad 3 into body cavity 2 through tube 1.

FIGS. 2–4 depict a particularly preferred embodiment of the invention, wherein pad 3 is an expandable member, as will be described in detail hereinafter. After being introduced into body cavity 2 through tube 1, pad 3 is unwound and expanded by being injected with a fluid 10. In addition to expanding pad 3, fluid 10, which preferably is a saline solution, weighs down pad 3 sufficiently to compress tissues and/or organs underlying pad 3, thereby providing a relatively unobstructed surgical field above pad 3.

As shown in FIGS. 2 and 3, pad 3 can be injected with fluid 10 through filling tube 11 connected between a one-way valve 12 on pad 3 and a fluid reservoir (not shown). After filling pad 3 with a desired volume of fluid 10, filling tube 11 can be separated from valve 12 and completely withdrawn from tube 1 or other tube/trocar through which filling tube 11 enters body cavity 2, to thereby free-up the tube/trocar as an access port for other laparoscopic instruments. Filling can also be accomplished by connecting the one-way valve 12 to a conventional aspirating device through a catheter.

As shown in FIGS. 2–4, pad 3 is a generally rectangular structure having rounded corners and an organ-isolating notch 7 in one edge thereof. Pad 3 preferably is formed of a pair of substrates 13 and 14 comprising any suitable flexible material(s), such as rubber, and the substrates are bonded together at transversely spaced apart, elongate regions 15. Each elongate region 15 preferably is interrupted by channels 16 in one or more locations to provide communication among the various compartments 160 formed between these elongate regions 15.

It should be understood that the peripheral edges of substrates 13 and 14 also are bonded together except at one portion thereof, at which there is provided a grasping tool passage 17. It should also be understood that the figures are not drawn to scale, and that the width of passage 17 is preferably much narrower than the widths of compartments 160. Grasping tool passage 17 preferably has a transverse dimension of approximately 6 mm, and provides a passage, or tunnel, for receiving a conventional 5 mm grasping tool 9 therein.

In order to facilitate rolling and unrolling pad 3 for passage through the tube or trocar, a grasping end 18 of grasping tool 9 is inserted into passage 17 and clamped to a projecting tab 19 connected to one of substrates 13 and 14 at the closed end of passage 17. Grasping tool 9 is then rotated to roll up pad 3. In order to maintain pad 3 in its rolled-up condition, complementary VELCRO® strips 20 and 21 are provided on external surfaces of substrates 13 and 14 which oppose each other when pad 3 is rolled-up in the same manner as described earlier in connection with the embodiment shown in FIGS. 1A–1D.

Figure 5:
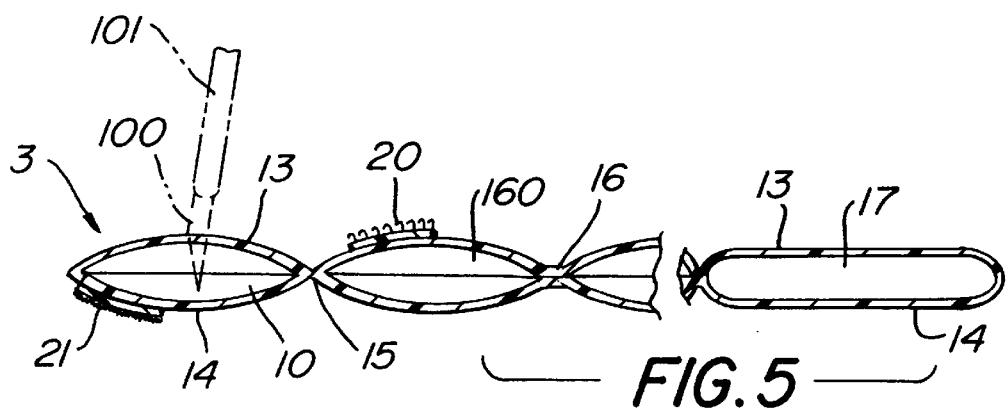
FIG. 5 is a cross-sectional view of an alternative embodiment of FIG. 3.

In an alternative embodiment shown in FIG. 5, the pad 3 can be filled with fluid 10 using a needle 100, which temporarily pierces a self-sealing surface of a substrate 13 of pad 3. Needle 100 is attached to a catheter or filling tube 101, which passes through the tube or trocar. After filling pad 3 with a desired volume of fluid 10, needle 100 and catheter 101 are preferably completely withdrawn from the tube or trocar, freeing-up the tube or trocar as an access port for other laparoscopic instruments. However, if desired, catheter 101 can be left in place and a conventional catheter closure can be employed to retain the liquid in the compression pad, or the needle and catheter assembly can be removed from the compression pad, since the surface material will self-seal.

In those embodiments wherein pad 3 is filled with fluid 10, pad 3 is removed from body cavity 2 at the end of the procedure, prior to closing, by substantially emptying fluid 10 from pad 3 before removing pad 3 from body cavity 2, grasping the substantially emptied pad 3 with a grasping tool 9 inserted through tube 1 (or another entry port), winding pad 3 about grasping tool 9, and pulling pad 3 and grasping tool 9 out of body cavity 2. When fluid 10 is physiologically compatible, e.g., normal saline solution, it can be emptied directly into body cavity 2 by opening a hole in pad 3. Such a hole can be created using any suitable means, such as a scalpel, scissors or any other cutting or piercing tool.

When fluid 10 is physiologically incompatible, it is suctioned out of pad 3 without contacting the patient with it. A suitable suction device can be connected to a piercing needle for removing fluid 10 from within the compression pad.

In the embodiments of the invention wherein pad 3 is expanded by fluid injection, at least one of substrates 13 and 14 can comprise a thin and flexible plastic layer, which can be, e.g., the same material used as a gall bladder holding bag in the Auto Suture Endo Catch®, as described in U.S. Pat. No. 5,074,867. Thus, suitable materials for pad 3 include rubber, and biologically inert flexible synthetic resin materials, such as polyethylene or nylon, which are impermeable to micro-organisms.

The shape of pad 3 in all embodiments is preferably rectangular, with rounded corners. It is particularly preferred to include an organ-isolating notch 7 in one edge thereof, as shown in the figures, to facilitate placement of pad 3 within body cavity 2. 20 In the preferred embodiment shown in FIG. 2, pad 3 includes a strip 8 of a heavy compound, such as lead or bismuth, provided along the length of notch 7 to add weight to the system.

In the most preferred embodiment, the external surface of the top substrate 13 of pad 3 is reflective, to aid in illuminating the site of the surgical procedure, and the bottom substrate 14 of pad 3 is roughened, such as is generally provided by a rubber substrate, to prevent pad 3 from inadvertently sliding within the body.

Fluid 10 preferably has a specific gravity substantially greater than 1 to ensure that pad 3 is heavy enough to pin down tissues and/or organs. The specific gravity of the fluid can be about 1 to about 14, preferably, at least about 2, more preferably, at least about 3. The fluid can comprise mercury, or any other heavy metal; however, it is preferred that such additives be nontoxic. Normal saline solution is the most preferred fluid.

Fluid 10 and filling tube 11 can combine to act as a fiber optic device, through which light is transmitted into body cavity 2 from outside the patient. Of course, in such an embodiment, it is advantageous to maintain the connection between filling tube 11 and valve 12 after filling pad 3 with fluid 10. As previously discussed, another way that lighting within body cavity 2 can be enhanced by the invention is by including reflective surfaces on pad 3 for enhancing the lighting within body cavity 2.

Figure 6:
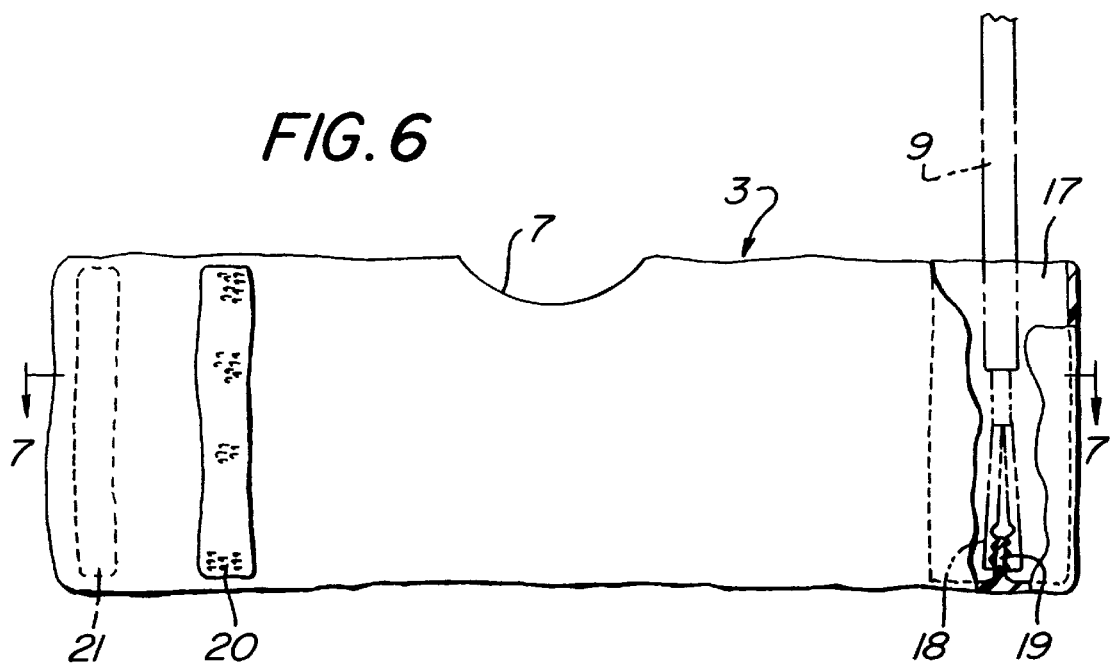
FIG. 6 is a plan view of yet another embodiment of the invention, with a portion of the top layer cut away to reveal underlying details.
Figure 7:
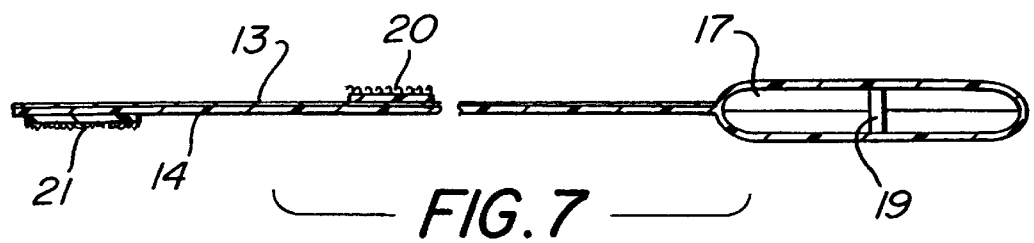
FIG. 7 is a cross-sectional view through line 7—7 of FIG. 6.

FIGS. 6 and 7 depict another embodiment of the invention, wherein pad 3 comprises a planar laminate of substrates 13 and 14, which can be fabric substrates. At least one of substrates 13 and 14 comprises a heavy material, such as lead or bismuth, which can be provided in a variety of forms, including, e.g., as fibers woven into the substrate or as a film. Substrates 13 and 14 should comprise materials sufficiently flexible to be rolled up for deployment and removal. Pad 3 is rolled up by grasping tab 19 in passage 17 with the grasping end 18 of grasping tool 9, and then rotating grasping tool 9 until VELCRO® tabs 20 and 21 engage one another. Pad 3 will then readily pass through a tube or trocar.

Unlike the embodiment depicted in FIG. 2, pad 3 of FIGS. 6 and 7 is not adapted to be filled with a fluid, since it is preweighted with a solid heavy material, such as bismuth or lead.

While the invention has been described in detail and with reference to specific examples thereof, it will be apparent to one skilled in the art that various changes and modifications can be made therein without departing from the spirit and scope thereof.

What is claimed is:

1. A method for eliminating tissue obstructions from a surgical field within a body cavity of a patient during laparoscopic/thorascopic surgery, said method comprising:

inserting a surgical compression pad for laparoscopic/thorascopic surgery into said body cavity through an access tube into said body cavity, wherein said pad is flexible and expandable;

expanding said pad to a shape for compressively contacting tissue adjacent to and underlying said surgical field, said shape being too large to pass unchanged through said tube;

compressively contacting tissue adjacent to and underlying said surgical field with said expanded compression pad to protectively separate and eliminate said adjacent tissue from said surgical field; and performing a surgical procedure in said surgical field while maintaining said expanded compression pad compressively contacting tissue adjacent to an underlying said surgical field.

2. A method for eliminating tissue obstructions from a surgical field within a body cavity of a patient during laparoscopic/thorascopic surgery, said method comprising:

providing a compression pad in the form of a sheet;

winding said compression pad around a deployment tool;

inserting said wound compression pad into said body cavity through an access tube into said body cavity, said pad being flexible and expandable;

unwinding said pad and thereby releasing said pad from said deployment tool after passing through said tube;

expanding said pad to a shape that is too large to pass unchanged through said tube; and contacting tissue adjacent to said surgical field with said expanded pad to separate and eliminate said adjacent tissue from said surgical field, said pad having a weight sufficient to displace said adjacent tissue from said surgical field; and removing said pad from said body cavity by grasping said pad with a grasping tool inserted through said tube, rewinding said pad about said grasping tool and pulling said grasping tool and pad out of said body cavity.

3. A method for eliminating tissue obstructions from a surgical field within a body cavity of a patient during laparoscopic/thorascopic surgery, said method comprising:

inserting a surgical compression pad for laparoscopic/thorascopic surgery into said body cavity through an access tube into said body cavity, said pad being a flexible and expandable fluid receiving packet;

expanding said pad to a shape that is too large to pass unchanged through said tube by injecting a fluid into said pad; and contacting tissue adjacent to said surgical field with said expanded pad to separate and eliminate said adjacent tissue from said surgical field.

4. The method of claim 3, wherein said pad comprises a self-sealing material through which said fluid is injected.

5. The method of claim 4, wherein said pad is inserted through said tube by pushing said pad through said tube with a deployment tool in contact with said pad, and said pad is freed from contact with said deployment tool after passing said pad through said tube.

6. The method of claim 3, further comprising removing said pad from said body cavity by substantially emptying said fluid from said pad before removing said pad from said body cavity, grasping said substantially emptied pad with a grasping tool inserted through said tube and pulling said pad and said grasping tool out of said body cavity.

7. The method of claim 6, wherein said emptied pad is wound around said grasping tool before being pulled out of said body cavity.

8. The method of claim 6, wherein said fluid is emptied into said body cavity by opening a hole in said pad and said fluid is physiologically compatible.

9. The method of claim 6, wherein said fluid is suctioned out of said pad without contacting said patient with said fluid.

10. The method of claim 9, wherein said fluid is physiologically incompatible.

11. The method of claim 6, wherein said fluid has a specific gravity of about 1 to about 14.

12. The method of claim 9, wherein said fluid has a specific gravity of at least about 2.

13. The method of claim 9, wherein said fluid has a specific of at least about 3.

14. The method of claim 6, wherein said fluid comprises mercury.

15. The method of claim 3, wherein said pad is attached to a fluid conduit through which said fluid is injected into said pad, and through which light is transmitted into said body cavity.

16. The method of claim 3, wherein said pad comprises a one-way valve into which said fluid is injected.

17. The method of claim 3, wherein said pad comprises a reflective face and a slip-resistant face.

18. The method of claim 3, wherein said pad comprises an organ isolating notch which is nestled against an organ during surgery.

19. The method of claim 18, wherein said pad further comprises a bismuth or lead strip along an edge of said notch.

20. A method for eliminating tissue obstructions from a surgical field within a body cavity of a patient during laparoscopic/thorascopic surgery, said method comprising:

providing a compression pad in the form of a sheet;

winding said compression pad around a deployment tool;

inserting the deployment tool with the compression pad wound thereon into said body cavity through an access tube into said body cavity, said pad being flexible and expandable, said pad comprising a reflective face and a slip-resistant face;

expanding said pad to a shape that is too large to pass unchanged through said tube; and contacting tissue adjacent to said surgical field with the slip-resistant face of said expanded pad to separate and eliminate said adjacent tissue from said surgical field, said pad having a weight sufficient to displace said adjacent tissue from said surgical field.

21. A method for eliminating tissue obstructions from a surgical field within a body cavity of a patient during laparoscopic/thorascopic surgery, said method comprising:

providing a compression pad in the form of a sheet;

winding said pad around a deployment tool;

inserting said tool with the pad wound therearound into said body cavity through an access tube into said body cavity, wherein said pad is flexible and expandable and comprises an organ isolating notch which is nestled against an organ during surgery;

expanding said pad to a shape that is too large to pass unchanged through said tube; and contacting tissue adjacent to said surgical field with said expanded pad to separate and eliminate said adjacent tube from said surgical field, said pad having a weight sufficient to displace said adjacent tissue from said surgical field.

22. The method of claim 21, wherein said pad further comprises a bismuth or lead strip along an edge of said notch.

23. A compression pad for laparoscopic and thorascopic surgery for eliminating tissue obstructions from a surgical field within a body cavity of a patient, said pad being capable of reversibly assuming at least two configuration; one of said at least two configurations being a contracted configuration in which said pad fits within and passes through an access tube inserted into a body cavity, and the other of said at least two configurations being an expanded configuration in which said pad cannot fit within or pass through said tube, said pad including a substantially rectangular sheet with an organ isolating notch along an edge thereof and a strip of at least one metal selected from the group consisting of lead and bismuth along an edge of said notch, wherein, at least in said expanded configuration, said pad is sufficiently heavy to compress tissue underlying said pad for isolating said tissue from a surgical field during surgery.

24. A compression pad for laparoscopic and thorascopic surgery for eliminating tissue obstructions from a surgical field within a body cavity of a patient, said pad being capable of reversibly assuming at least two configurations; one of said at least two configurations being a contracted configuration in which said pad fits within and passes through an access tube inserted into a body cavity, and the other of said at least two configurations being an expanded configuration in which said pad cannot fit within or pass through said tube, wherein said pad comprises at least one metal selected from the group consisting of lead and bismuth, wherein, at least in said expanded configuration, said pad is sufficiently heavy to compress tissue underlying said pad for isolating said tissue from a surgical field during surgery.

25. A compression pad for laparoscopic and thorascopic surgery for eliminating tissue obstructions from a surgical field within a body cavity of a patient, said pad being capable of reversibly assuming at least two configurations; one of said at least two configurations being a contracted configuration in which said pad fits within and passes through an access tube inserted into a body cavity, and the other of said at least two configurations being an expanded configuration in which said pad cannot fit within or pass through said tube, wherein said pad comprises a reflective face and a slip-resistant face, wherein, at least in said expanded configuration, said pad is sufficiently heavy to compress tissue underlying said pad for isolating said tissue from a surgical field during surgery.

26. A compression pad for laparoscopic and thorascopic surgery for eliminating tissue obstructions from a surgical field within a body cavity of a patient, said pad being capable of reversibly assuming at least two configurations; one of said at least two configurations being a contracted configuration in which said pad fits within and passes through an access tube inserted into a body cavity, and the other of said at least two configurations being an expanded configuration in which said pad cannot fit within or pass through said tube, wherein said pad comprises fasteners on surfaces that oppose each other when said pad is in said contracted configuration, said fasteners being adapted to reversibly engage each other to reversibly maintain said pad in said contracted configuration, wherein, at least in said expanded configuration, said pad is sufficiently heavy to compress tissue underlying said pad for isolating said tissue from a surgical field during surgery.

27. A compression pad for laparoscopic and thorascopic surgery for eliminating tissue obstructions from a surgical field within a body cavity of a patient, said pad being capable of reversibly assuming at least two configurations; one of said at least two configurations being a contracted configuration in which said pad fits within and passes through an access tube inserted into a body cavity, and the other of said at least two configurations being an expanded configuration in which said pad cannot fit within or pass through said tube, wherein said pad comprises two flexible substrates bonded together at transversely spaced apart, elongate regions interrupted by channels, said two flexible substrates also are bonded together along entire peripheries thereof, except at an end of said pad at which there is a grasping tool passage with a tab for grasping therein, wherein, at least in said expanded configuration, said pad is sufficiently heavy to compress tissue underlying said pad for isolating said tissue from a surgical field during surgery.

28. A compression pad for laparoscopic and thorascopic surgery for eliminating tissue obstructions from a surgical field within a body cavity of a patient, said pad being capable of reversibly assuming at least two configurations; one of said at least two configurations being a contracted configuration in which said pad fits within and passes through an access tube inserted into a body cavity, and the other of said at least two configurations being an expanded configuration in which said pad cannot fit within or pass through said tube, wherein said pad comprises two flexible substrates bonded together at transversely spaced apart, elongate regions interrupted by channels, and at peripheral edges of said substrates, and wherein said bonded substrates define a fluid holding cavity therebetween, said pad being in a form of a substantially rectangular sheet with an organ isolating notch along an edge thereof, wherein, at least in said expanded configuration, said pad is sufficiently heavy to compress tissue underlying said pad for isolating said tissue from a surgical field during surgery.

29. The compression pad of claim 28, wherein a strip of at least one metal selected from the group consisting of lead and bismuth is along an edge of said notch.

30. A compression pad for laparoscopic and thorascopic surgery for eliminating tissue obstructions from a surgical field within a body cavity of a patient, said pad being capable of reversibly assuming at least two configurations; one of said at least two configurations being a contracted configuration in which said pad fits within and passes through an access tube inserted into a body cavity, and the other of said at least two configurations being an expanded configuration in which said pad cannot fit within or pass through said tube, wherein said pad comprises two flexible substrates bonded together at transversely spaced apart, elongate regions interrupted by channels, and at peripheral edges of said substrates, and wherein said bonded substrates define a fluid holding cavity therebetween, one of said substrates having a reflective face and the other of said substrates having a slip-resistant face, wherein, at least in said expanded configuration, said pad is sufficiently heavy to compress tissue underlying said pad for isolating said tissue from a surgical field during surgery.

31. A compression pad for laparoscopic and thorascopic surgery for eliminating tissue obstructions from a surgical field within a body cavity of a patient, said pad being capable of reversibly assuming at least two configurations; one of said at least two configurations being a contracted configuration in which said pad fits within and passes through an access tube inserted into a body cavity, and the other of said at least two configurations being an expanded configuration in which said pad cannot fit within or pass through said tube, wherein said pad comprises two flexible substrates bonded together at transversely spaced apart, elongate regions interrupted by channels, and at peripheral edges of said substrates, and wherein said bonded substrates define a fluid holding cavity therebetween, said pad comprising fasteners on surfaces that oppose each other when said pad is in said contracted configuration, said fasteners being adapted to reversibly engage each other to reversibly maintain said pad in said contracted configuration, wherein, at least in said expanded configuration, said pad is sufficiently heavy to compress tissue underlying said pad for isolating said tissue from a surgical field during surgery.

* * * * *